United States Patent [19]

Madgavkar et al.

[11] 4,213,001

[45] Jul. 15, 1980

[54] OLIGOMERIZING ALPHA-OLEFINS WITH A HETEROGENEOUS CATALYST

[75] Inventors: Ajay M. Madgavkar, Pittsburgh; Harold E. Swift, Gibsonia; Barrett L. Cupples, Franklin Township, Westmoreland County, all of Pa.

[73] Assignee: Gulf Research and Development Company, Pittsburgh, Pa.

[21] Appl. No.: 955,210

[22] Filed: Oct. 27, 1978

[51] Int. Cl.$^2$ ............................................. C07C 3/18
[52] U.S. Cl. .................................... 585/510; 585/525
[58] Field of Search ................. 260/683.15; 585/510, 585/525

[56] References Cited

U.S. PATENT DOCUMENTS

| 2,657,245 | 10/1953 | Davidson | 260/683.15 B |
| 2,766,312 | 10/1956 | Serniuk | 260/683.15 B |

Primary Examiner—C. Davis

[57] ABSTRACT

A method of homopolymerizing a 1-olefin to a product including the trimer and tetramer by utilizing boron trifluoride under pressure in the presence of a suspended particulate adsorbent material. For example, 1-decene is homopolymerized at a temperature of about 25° C. in the presence of a suspension of about two weight percent silica and boron trifluoride at a pressure of 125 psi.

11 Claims, No Drawings

OLIGOMERIZING ALPHA-OLEFINS WITH A HETEROGENEOUS CATALYST

SUMMARY OF THE INVENTION

An alpha-olefin such as 1-decene is oligomerized to a product predominating in the trimer and tetramer using boron trifluoride under pressure as the catalyst in the presence of a slurry of a particulate adsorbent material such as silica.

DESCRIPTION OF THE INVENTION

The oligomers of certain 1-olefins that have been polymerized using boron trifluoride as the catalyst are highly useful as base fluids for preparing lubricants, hydraulic fluids, transmission fluids, transformer fluids, and the like, generically designated by the term functional fluids. The oligomer product of 1-decene is particularly preferred but the oligomerization of mixtures of 1-decene with other 1-olefins having from six to 12 carbon atoms are also useful for preparing these functional fluids.

These functional fluids are prepared with various proportions of the 1-olefin trimer, tetramer and pentamer fractions. Since the dimer possesses significant volatility and low viscosity, it is separated out from the oligomerization product mixture for separate use or disposal.

The use of a promoter or co-catalyst with the boron trifluoride is conventional in order to obtain useful catalytic activity for the boron trifluoride. The co-catalyst complexes with the boron trifluoride to form a coordination compound which is catalytically active for the oligomerization reaction. Included in the list of substances which have been recommended as co-catalysts are aliphatic ethers, such as dimethyl ether and diethyl ether; aliphatic alcohols, such as methanol, ethanol, n-butanol and decanol; polyols, such as ethylene glycol and glycerol; water; aliphatic carboxylic acids, such as acetic acid, propanoic acid and butyric acid; esters, such as ethyl acetate and methyl propionate; ketones, such as acetone; aldehydes, such as acetaldehyde and benzaldehyde and acid anhydrides, such as acetic acid anhydride and succinic anhydride. The use of these boron trifluoride coordination compounds is described in U.S. Pat. Nos. 3,149,178; 3,382,291; 3,742,082; 3,763,244; 3,769,363; 3,780,128; 3,997,621; 4,045,507 and others.

Although these coordination compounds of boron trifluoride are very effective oligomerization catalysts for the higher alpha-olefins, they present a serious catalyst recovery and disposal problem. Experiments that have been carried out demonstrate that these coordination compounds possess a significantly reduced activity when they are recovered in the product stream and recycled to the reactor feed stream. Therefore, fresh catalyst and co-catalyst must be used and the spent catalyst must be separated out from the oligomerization product and disposed. The cost of new catalyst and of waste treatment including disposal procedures designed to prevent environmental contamination can make this process prohibitive.

We have discovered a catalyst system which avoids these catalyst disposal problems of existing boron trifluoride catalyzed processes and which can direct the oligomerization to an oligomer yield which is high in the particularly desirable trimer fraction. In our process a powdered solid adsorbent is suspended in the alpha-olefin monomer by suitable agitation of the reaction liquid. The reaction vessel is pressured with boron trifluoride gas and the oligomerization reaction proceeds. The product stream is filtered to recover the powdered adsorbent and the boron trifluoride is stripped from the product stream by moderate heating. Both of these can then be recycled for reuse. We have found that the conversion and oligomer distribution obtained by our process can be significantly affected by a number of factors including the boron trifluoride partial pressure, the oligomerization temperature, the type of adsorbent and its concentration and the length of time over which the oligomerization reaction is carried out.

As is the case with the prior art oligomerizations, 1-decene is the most preferred alpha-olefin for preparing synthetic lubricants and related functional fluids by our novel process. However, various combinations of alpha-olefins having from six to 12 carbon atoms and preferably eight to 12 carbon atoms can also be used.

Any adsorbent material, inorganic or organic, which has a surface area of at least about 0.1 $m^2/g$. and which is insoluble in the reaction liquid can be used as the solid adsorbent in our process. The class of inorganic adsorbents includes silica, the silica-aluminas, silica-zirconia, silica-magnesia, silica-thoria, alumina, magnesia, zirconia, activated carbon, the zeolites, silicon carbide, silicon nitride, titania, aluminum-aluminum phosphate, zirconium phosphate, thoria, the magnesia-aluminas, such as magnesium aluminate, zinc aluminate, pumice, naturally occurring clays, such as diatomaceous earth, and the like. The class of organic adsorbents includes porous polyvinyl alcohol beads, porous polyethylene glycol beads, the macroreticular acid cation exchange resins, such as the sulfonated styrene-divinylbenzene copolymer exchange resins (for example, Amberlyst-15 and Amberlite-XN1040 supplied by Rohm and Haas Company, Philadelphia, Pa.), and the like. We prefer silica or a composition predominating in silica as the solid adsorbent. This solid adsorbent is used in a finely divided form to permit its suspension and despersion throughout the reaction liquid by appropriate agitation. The particle size of the solid adsorbent is, in part, dependent on its specific gravity and on the vigor of the agitation, which is used. In general, a useful particle size will be between about 3 and about 400 mesh (0.075-6.7 mm.) and more preferably between about 8 and about 100 mesh (0.15-2.4 mm.) and most preferably between about 10 and about 50 mesh (0.3-2.0 mm.).

We have found that the concentration of the solid adsorbent in the reaction liquid is a variable which exerts a significant effect on the rate of the oligomerization reaction and on the selectivity to the various oligomer fractions. Thus, as the amount of the adsorbent is increased, the reaction rate increases but the selectivity to the desired trimer decreases. Therefore, the concentration of the adsorbent is controlled in order to obtain a suitable yield of the trimer. We have found that a useful product distribution is obtained when the reaction liquid contains between about 0.1 and about 20 weight percent of the solid adsorbent and preferably between about 0.5 and about 10 percent.

We have further found that the pressure of the boron trifluoride in the reaction vessel exerts a significant effect on the oligomerization reaction. Thus, as the boron trifluoride pressure increases, the selectivity to the higher oligomer fractions including the tetramer and pentamer increases and the selectivity to the dimer decreases. Therefore, we find that a boron trifluoride pressure of between about 5 psig. (135 kPa) and about 1,000 psig. (7,000 kPa) will produce a useful product but we prefer that the boron trifluoride pressure be between about 50 (445 kPa) and about 500 psig. (3,540 kPa) for the more desirable product distribution and we most prefer a pressure between about 75 (618 kPa) and about 300 psig. (2,170 kPa). The boron trifluoride pressure can be suitably controlled within these ranges to optimize a desired product distribution. As used herein, the boron trifluoride pressure refers to the partial pressure of boron trifluoride in the free space of the reaction vessel if an inert diluent gas is also present in the reaction vessel. But since an inert diluent gas is not necessary, the boron trifluoride gas will generally be the only significant gaseous component in the reaction vessel.

The reaction temperature is also an important variable with regard to the product distribution. Thus, we have found that the selectivity to dimer decreases and the selectivity to the trimer increases as the reaction temperature is lowered. The oligomerization reaction can be carried out at a temperature between about $-50°$ C. and about 150° C. but a temperature range between about $-30°$ C. and about 50° C. is preferred and a range between about $-10°$ C. and about 30° C. is most preferred.

Time is a significant factor in the overall reaction for several reasons. First, after the reactor containing the 1-olefin and the suspended solid adsorbent at reaction temperature is pressured with boron trifluoride, there is a delay, generally of about five to about 30 minutes depending on conditions, until substantial conversion of the alpha-olefin is evidenced. Since this delayed reaction is also accompanied by a substantial pressure drop, the delay is attributed to the adsorption of boron trifluoride onto the adsorbent. Therefore, sufficient time must be provided for this adsorption process.

Furthermore, the overall result is the product of many concurrent reactions occurring at different rates and differently affected by variations in the reaction parameters. For example, while monomer dimerizes to dimer and dimer dimerizes to tetramer, the monomer reacts with dimer to form trimer. Thus, if the monomer dimerizes so rapidly that monomer is quickly exhausted, then the reaction and yield to trimer will be relatively low and cannot be increased with time. But the reaction of dimer to tetramer can significantly increase with time. And the reaction of dimer with trimer to form pentamer will cause the actual decrease of trimer with time. Therefore, we have discovered that the optimization of trimer demands the careful correlation of all reaction parameters. As a result, we have found that although a reaction time of between about five minutes and five hours can produce a useful product, we prefer a reaction time within a time of between about 20 minutes and three hours and most preferably between about 30 minutes and two hours.

The expression reaction liquid as used herein refers to the alpha-olefin monomer or mixture of monomers before the initiation of the reaction and the monomer and oligomer products during the course of the reaction in the preferred form of the reaction. However, it is also possible to carry out the reaction in the presence of up to about 80 percent, preferably up to about 60 percent, of a suitable inert solvent. Such solvents tend to slow down the various reaction rates and can be utilized in conjunction with the different variables to control the course of the reaction and the nature of the reaction products. Suitable solvents can be selected from aliphatic hydrocarbons such as pentane, hexane, heptane, and the like; and aromatic hydrocarbons, such as benzene, toluene, chlorobenzene, and the like. The solvent, if utilized, should be liquid at reaction conditions and should be substantially lower in boiling point than any other component to simplify separation upon completion of the reaction.

The process as described is a batch process in which the components are added to a closed reaction vessel such as an autoclave at the beginning of the reaction. During reaction the reactor contents are stirred to ensure uniform dispersion and boron trifluoride is injected as required to maintain the desired pressure. All components are removed and separated at the conclusion of the reaction and the cycle is repeated including the recycle of the recovered solid adsorbent and boron trifluoride.

The reaction can also be run continuously in an autoclave by the use of appropriate equipment modifications. In this continuous procedure, a suitable porous filter plate is positioned between the reaction liquid and the reactor outlet. A continuous stream of reaction product is removed at a rate to provide a predetermined desirable average residence time. Since the filter plate prevents the egress of the powdered adsorbent, the product stream is free of solids. As the product is removed, make-up alpha-olefin is injected into the reactor at the same rate as the product is removed to provide a constant liquid volume in the reactor. The particle size of the adsorbent, the openings in the filter plate and the vigor of the agitation are appropriately intercorrelated to ensure that the adsorbent particles neither block the filter openings nor cake up on the filter plate. And, as with the batch method, a predetermined desirable boron trifluoride pressure is maintained in the reactor.

In another procedure the slurry is flowed through an elongated tube reactor while the desired boron trifluoride pressure is maintained in the reactor. A flow rate is maintained to provide the desired residence time in the reactor. The product stream is then separated as in the batch process and the recovered solid adsorbent and boron trifluoride are recycled.

DESCRIPTION OF PREFERRED EMBODIMENTS

The following experiments were carried out in a two liter stainless steel autoclave equipped with a cooling coil and a magnetic stirrer. The reactor was also equipped with a sample line in the form of a loop which contained a pump for continuously withdrawing and recirculating a stream of the reaction mixture. Two to five cc. samples were removed periodically for analysis after the boron trifluoride had been removed. Analysis was by gas chromatograph up to a sample temperature of about 390° C. The silica used in the following experiments, except where noted otherwise, was calcined at 1000° F. (537° C.), had a particle size of between about 10 and 20 mesh (0.8 and 2.0 mm.) and had a surface area of about 250 m$^2$/g. with an average pore radius under 100 angstroms. All experiments used 500 g. of 1-decene.

The first series of experiments, Examples 1–4, was carried out to determine if the amount of silica that was slurried in the reaction liquid was significant.

EXAMPLE 1

The 1-decene and 10 g. of the silica were introduced into the reactor. After the cooling, water was started to maintain a constant temperature of 23° C., the reactor was pressured with boron trifluoride to a constant pressure of 125 psig. (962 kPa). The results of periodic analyses of the reaction liquid including percent selectivities to the various oligomer fractions are set out in Table I with time being in minutes.

Table I

| Time | Conv. % | $C_{20}$ | $C_{30}$ | $C_{40}$ | $C_{50}$ |
|---|---|---|---|---|---|
| 20 | 32.1 | 44.7 | 48.5 | 6.8 | — |
| 30 | 43.4 | 35.5 | 53.8 | 9.3 | 1.4 |
| 60 | 70.3 | 27.4 | 59.1 | 12.6 | 0.9 |
| 120 | 83.3 | 25.9 | 58.8 | 13.6 | 1.8 |
| 180 | 89.5 | 25.7 | 56.7 | 15.1 | 2.6 |
| 240 | 92.9 | 25.4 | 58.0 | 15.5 | 1.1 |
| 300 | 94.5 | 23.9 | 58.9 | 17.1 | 0.2 |

EXAMPLE 2

Example 1 was repeated with 20 g. of silica. The results are set out in Table II.

Table II

| Time | Conv. % | $C_{20}$ | $C_{30}$ | $C_{40}$ | $C_{50}$ |
|---|---|---|---|---|---|
| 30 | 50.1 | 35.2 | 55.3 | 8.7 | 0.85 |
| 60 | 71.9 | 30.8 | 55.4 | 12.0 | 1.9 |
| 180 | 91.2 | 29.1 | 53.2 | 14.8 | 2.9 |
| 300 | 93.2 | 27.9 | 54.6 | 15.3 | 2.2 |

EXAMPLE 3

Example 1 was repeated using 50 g. of silica. These results are set out in Table III.

Table III

| Time | Conv. % | $C_{20}$ | $C_{30}$ | $C_{40}$ | $C_{50}$ |
|---|---|---|---|---|---|
| 30 | 75.3 | 38.6 | 51.9 | 9.1 | 0.4 |
| 60 | 86.6 | 36.7 | 52.3 | 10.8 | 0.2 |
| 180 | 92.6 | 32.9 | 53.6 | 13.0 | 0.6 |
| 300 | 94.2 | 28.0 | 51.5 | 17.4 | 3.1 |

EXAMPLE 4

Example 1 was repeated using 150 g. of silica. These results are set out in Table IV.

Table IV

| Time | Conv. % | $C_{20}$ | $C_{30}$ | $C_{40}$ | $C_{50}$ |
|---|---|---|---|---|---|
| 180 | 87.1 | 47.4 | 41.1 | 11.0 | 1.1 |
| 300 | 92.6 | 26.1 | 40.0 | 26.0 | 7.9 |

The next series of experiments as set out in Examples 5-8 was carried out to evaluate the effect of boron trifluoride pressure on the product distribution.

EXAMPLE 5

Example 2 was repeated except that the pressure of boron trifluoride in the reactor during the course of the reaction was 200 psig. (1,480 kPa). The results are set out in Table V.

Table V

| Time | Conv. % | $C_{20}$ | $C_{30}$ | $C_{40}$ | $C_{50}$ |
|---|---|---|---|---|---|
| 60 | 92.2 | 24.1 | 49.9 | 19.4 | 6.7 |
| 180 | 95.2 | 25.2 | 47.1 | 18.8 | 8.9 |
| 300 | 95.6 | 21.8 | 46.3 | 20.8 | 11.1 |

EXAMPLE 6

Example 2 was repeated using a boron trifluoride pressure of 500 psig. (3,540 kPa). The results are set out in Table VI.

Table VI

| Time | Conv. % | $C_{20}$ | $C_{30}$ | $C_{40}$ | $C_{50}$ |
|---|---|---|---|---|---|
| 30 | 74.4 | 12.6 | 43.5 | 28.6 | 15.3 |
| 60 | 89.6 | 10.7 | 38.8 | 31.0 | 19.4 |
| 180 | 93.3 | 9.4 | 28.8 | 33.0 | 28.9 |

EXAMPLE 7

The reaction was carried out using a boron trifluoride pressure of 50 psig. (445 kPa) and 50 g. of silica at a temperature of 75° C. The results are set out in Table VII.

Table VII

| Time | Conv. % | $C_{20}$ | $C_{30}$ | $C_{40}$ | $C_{50}$ |
|---|---|---|---|---|---|
| 30 | 89.4 | 62.3 | 30.0 | 7.4 | 0.3 |
| 60 | 92.6 | 54.4 | 32.0 | 12.0 | 1.6 |
| 180 | 92.7 | 49.8 | 34.3 | 15.4 | 0.6 |
| 300 | 93.3 | 42.4 | 33.7 | 20.5 | 3.4 |

EXAMPLE 8

Example 7 was repeated except that the boron trifluoride pressure was reduced to 10 psig. (170 kPa). The results are set out in Table VIII.

Table VIII

| Time | Conv. % | $C_{20}$ | $C_{30}$ | $C_{40}$ | $C_{50}$ |
|---|---|---|---|---|---|
| 30 | 58.1 | 67.4 | 29.2 | 3.4 | — |
| 60 | 61.4 | 67.3 | 28.8 | 3.7 | 0.3 |
| 120 | 80.5 | 63.0 | 30.7 | 5.9 | 0.4 |

EXAMPLE 9

The effect of temperature on the reaction was studied in this experiment. Example 2 was repeated except that the reaction was carried out at a temperature of 60° C. The results are set out in Table IX.

Table IX

| Time | Conv. % | $C_{20}$ | $C_{30}$ | $C_{40}$ | $C_{50}$ |
|---|---|---|---|---|---|
| 30 | 62.5 | 41.0 | 50.2 | 8.1 | 0.7 |
| 60 | 86.5 | 52.5 | 39.3 | 8.2 | 0.3 |
| 180 | 93.5 | 47.2 | 37.2 | 13.9 | 1.8 |
| 300 | 94.0 | 38.9 | 39.4 | 18.8 | 2.9 |

EXAMPLE 10

An experiment was carried out to determine the effect of surface area on the distribution of the oligomerization reaction products. Example 7 was repeated except that the silica was calcined at a temperature of 1,980° F. (1,082° C.). As a result of this calcination, the surface area of the silica decreased from about 250 m²/g. to less than one m²/g. The results are set out in Table X.

Table X

| Time | Conv. % | $C_{20}$ | $C_{30}$ | $C_{40}$ | $C_{50}$ |
|---|---|---|---|---|---|
| 30 | 24.9 | 59.2 | 34.1 | 6.2 | 0.6 |
| 60 | 41.8 | 54.1 | 38.7 | 6.2 | 1.0 |
| 180 | 81.9 | 62.6 | 31.5 | 5.9 | 0.03 |

EXAMPLE 11

In this experiment 500 g. of 1-decene and 50 g. of a 40 to 50 mesh (0.3 to 0.4 mm.) silica, which has been impregnated with boric acid to contain one weight percent boron and impregnated with hydrogen fluoride to contain 5.28 percent fluorine, were used. The impregnated silica was calcined to 1,650° F. (900° C.). The reaction was carried out at 120° C. without boron trifluoride at atmospheric pressure. After two hours of reaction, the conversion of 1-decene was 2.46 percent at a distribution of 92.3 percent dimer and 7.7 percent trimer.

EXAMPLE 12

Example 11 was repeated except that the reactor was pressured to 50 psig. (445 kPa) with boron trifluoride. After two hours, the conversion was 62.4 percent at a selectivity of 76.4 percent to dimer, 20.3 percent to trimer, 3.3 percent to tetramer and 0.05 percent to pentamer.

EXAMPLE 13

The reactor was charged with 500 g. of 1-decene and 50 g. of 10 to 20 mesh pseudoboehmite alumina having an average pore diameter of about 50 angstroms. The reactor was pressured to 125 psig. (965 kPa) with boron trifluoride while a temperature of 23° C. was maintained in the reactor. After one hour, analysis revealed that there was 53.3 percent conversion at a selectivity of 49.5 percent to dimer, 37.0 percent to trimer, 11.6 percent to tetramer and 1.8 percent to pentamer. The boron trifluoride pressure was then raised to 500 psig. (3,540 kPa). Two and one-half hours later analysis showed that there was an overall 88.4 percent conversion at a selectivity of 42.3 percent to dimer, 39.9 percent to trimer, 16.2 percent to tetramer and 1.6 percent to pentamer.

EXAMPLE 14

Example 13 was repeated except that the pseudoboehmite was replaced by 50 g. of an alumina having an average pore diameter of about 200 angstroms. After one hour, there was 53.6 percent conversion at a selectivity of 46.8 percent to dimer, 40.1 percent to trimer, 11.2 percent to tetramer and 1.9 percent to pentamer. After two and one-half hours at the higher boron trifluoride pressure, there was an overall conversion of 92.3 percent at a selectivity of 32.7 percent to dimer, 43.1 percent to trimer, 19.8 percent to tetramer and 4.45 percent to pentamer.

EXAMPLE 15

An experiment was carried out using 300 g. of 1-decene and 30 g. of several 40 to 50 mesh (0.3 to 0.4 mm.) solid adsorbents and comparing these results with an experiment in which no solid adsorbent was used. In all experiments the pressure of boron trifluoride was 50 psig. (445 kPa) and the temperature was about 75° C. The results of an analysis of each product after 30 minutes of reaction are set out in Table XI.

Table XI

| Adsorbent | Conv. % | $C_{20}$ | $C_{30}$ | $C_{40}$ | $C_{50}$ |
|---|---|---|---|---|---|
| blank | 3.73 | 69.0 | 19.0 | 7.2 | 1.6 |
| silica | 86.7 | 68.3 | 26.7 | 4.8 | 0.2 |
| alumina | 86.5 | 87.0 | 11.4 | 1.5 | 0.04 |
| pva[a] | 87.7 | 62.8 | 30.7 | 6.4 | 0.2 |
| AMB-15[b] | 80.7 | 74.7 | 22.7 | 2.6 | — |

[a] porous polyvinyl alcohol beads
[b] Amberlyst-15, a sulfonated styrene-divinylbenzene copolymer exchange resin It is to be understood that the above disclosure is by way of specific example and that numerous modifications are available to those of ordinary skill in the art without departing from the true spirit and scope of the invention.

We claim:

1. The process for oligomerizing an alpha-olefin having from six to twelve carbon atoms and mixtures thereof which comprises contacting a mixture consisting essentially of said alpha-olefin and a suspension of a powdered solid adsorbent having a surface area of at least about 0.1 m$^2$/g. at a temperature between about −50° and about 150° C. with boron trifluoride at a pressure between about 5 and about 1,000 psig. (about 135 and about 7,000 kPa).

2. The process for oligomerizing an alpha-olefin in accordance with claim 1 in which the solid adsorbent has a particle size between about 3 and about 400 mesh (about 0.075 and about 6.7 mm.).

3. The process for oligomerizing an alpha-olefin in accordance with claim 1 in which the solid adsorbent comprises from about 50 to 100 percent silica.

4. The process for oligomerizing an alpha-olefin in accordance with claim 1 in which the reaction comprises between about 0.1 and about 20 percent of said solid adsorbent.

5. The process for oligomerizing an alpha-olefin in accordance with claim 1 in which the pressure of boron trifluoride is between about 50 and about 500 psig. (about 445 and about 3,540 kPa).

6. The process for oligomerizing an alpha-olefin in accordance with claim 1 in which the temperature is between about −30° and about 50° C.

7. The process for oligomerizing an alpha-olefin in accordance with claim 1 in which the alpha-olefin is 1-decene.

8. The process for oligomerizing an alpha-olefin in accordance with claim 1 in which the reaction is carried out as a batch reaction for a period of time between about five minutes and about five hours.

9. The process for oligomerizing an alpha-olefin in accordance with claim 1 in which the alpha-olefin is flowed through the reactor in contact with the suspension of powdered solid adsorbent at a rate to provide an average contact time of between about 30 minutes and about two hours.

10. The process for oligomerizing an alpha-olefin in accordance with claim 1 in which the solid adsorbent has a particle size between about 10 and about 50 mesh (about 0.3 and about 2.0 mm.).

11. The process for oligomerizing 1-decene to a product predominant in the trimer of 1-decene which comprises contacting a mixture of 1-decene and between about 0.5 and about ten weight percent of a suspension of powdered silica at a temperature of between about −10° and about 30° C. with boron trifluoride under a pressure of between about 75 and about 300 psig. (about 618 and about 2,170 kPa).

* * * * *